United States Patent [19]
Foguet et al.

[11] Patent Number: 5,973,155
[45] Date of Patent: *Oct. 26, 1999

[54] PROCESS FOR PREPARING (−)-TRANS-N-P-FLUOROBENZOYLMETHYL-4-(P-FLUOROPHENYL)-3-[[3,4-(METHYLENEDIOXY)PHENOXY]METHYL]-PIPERIDINE

[75] Inventors: Rafael Foguet; Santiago Gubert; Aurelio Sacristan; José A. Ortiz, all of Barcelona, Spain

[73] Assignee: Ferrer Internacional, S.A., Barcelona, Spain

[ * ] Notice: This patent is subject to a terminal disclaimer.

[21] Appl. No.: 08/945,442

[22] PCT Filed: Feb. 28, 1997

[86] PCT No.: PCT/EP97/01007

§ 371 Date: Oct. 27, 1997

§ 102(e) Date: Oct. 27, 1997

[87] PCT Pub. No.: WO97/31915

PCT Pub. Date: Sep. 4, 1997

[30] Foreign Application Priority Data

Feb. 29, 1996 [ES] Spain ..................................... 9600481

[51] Int. Cl.$^6$ ...................... A61K 31/445; C07D 405/12
[52] U.S. Cl. ............................................ 546/197; 514/321
[58] Field of Search ............................. 546/197; 514/321

[56] References Cited

U.S. PATENT DOCUMENTS 5,665,736  9/1997  Foguit et al. ............................ 514/321

OTHER PUBLICATIONS

Berge et al. "Pharmaceutical salts" J. PHarm. Sci. V. 66, pp. 1–2, 1977.

*Primary Examiner*—Ceila Chang
*Attorney, Agent, or Firm*—Birch, Stewart, Kolasch & Birch, LLP

[57] ABSTRACT

The process consists of reacting (−)trans-N-p-fluorophenyl)-3-[[3,4-(methylenedioxy)phenoxy]methyl]-piperidine acetate with 2-chloro- or 2-bromo-4'-fluoroacetophenone. The resulting compound can be isolated as a pharmaceutically acceptable addition salt by reaction with the corresponding acid.

8 Claims, No Drawings

PROCESS FOR PREPARING (−)-TRANS-N-P-FLUOROBENZOYLMETHYL-4-(P-FLUOROPHENYL)-3-[[3,4-(METHYLENEDIOXY)PHENOXY]METHYL]-PIPERIDINE

This application is a 371 National Stage of PCT/EP97/01007, filed Feb. 28, 1997.

The present invention relates to a new process for preparing (−)-trans-N-p-fluorobenzoylmethyl-4-(p-fluorophenyl)-3-[[3,4-(methylenedioxy)phenoxy]methyl]-piperidine as well as its pharmaceutically acceptable addition salts.

WO 95/25732 describes the aforesaid compound and its hydrochloride, which is the preferred salt for its therapeutic use. These compounds inhibit 5-hydroxytryptamine reuptake and are surprisingly less toxic than analogous compounds commonly used in therapeutics. Consequently, they are potentially useful in the treatment of depression.

In WO 95/25732 the compound (−)-trans-N-p-fluorobenzoyl-methyl-4-(p-fluorophenyl)-3-[[(3,4-(methylenedioxy)phenoxy]methyl]-piperidine is prepared by reacting (−)-trans-4-(p-fluorophenyl)-3-[[3,4-(methylenedioxy)phenoxy]methyl]-piperidine hydrochloride with 2-chloro- or 2-bromo-4'-fluoroacetophenone in an anhydrous alcohol medium, such as that constituted by methanol or ethanol, and in the presence of a mineral base, such as alkali metal carbonates or bicarbonates, that facilitates the uptake reaction of the formed hydracid.

Under these conditions, the reaction product must be separated from the decomposition products by column chromatography, which involves a considerably prolonged operating time as well as a decreased yield that hardly reaches 60%. In addition, the reaction by-products are difficult to remove and their presence has negative repercussions on the samples obtained.

Applicants have surprisingly found out that if instead of starting from (−)-trans-4-(p-fluorophenyl)-3-[[3,4-(methylenedioxy)phenoxy]methyl]-piperidine hydrochloride salt the corresponding acetate is used, the solvent ratio can be decreased due to a higher solubility of the acetate in organic solvents. Furthermore, purification of the reaction product by column chromatography is unnecessary, and the resulting product can be directly isolated as a pharmaceutically acceptable addition salt, e.g. as hydrochloride. This provides a significantly higher yield and enhances the purity of the final product. These factors become determinant in the industrial production and constitute the main advantages of the new process disclosed in the present invention.

Thus, the present invention relates to a process for preparing (−)-trans-N-p-fluorobenzoylmethyl-4-(p-fluorophenyl)-3-[[3,4-(methylenedioxy)phenoxy]methyl]-piperidine, as well as pharmaceutically acceptable addition salts thereof, which comprises reacting (−)-trans-(p-fluorophenyl)-3-[[3,4-(methylenedioxy)phenoxy]methyl]-piperidine acetate with 2-chloro (or bromo)-4'-fluoroacetophenone, preferably 2-chloro-4'-fluoroacetophenone, in an alcohol having 1 to 4 carbon atoms and in the presence of a base at an elevated temperature of the mixture, and if desired, converting the resulting compound to a pharmaceutically acceptable addition salt by reaction with the corresponding acid.

Among solvents suitable to carry out the above alkylation reaction, alkanols are preferred. Advantageously employed are those alkanols having one to four carbon atoms, such as methanol, ethanol, 1-propanol, 2-propanol, 1-butanol, 2-butanol or 2-methylpropan-1-ol. Especially preferred are methanol and/or ethanol. Mixtures of the above solvents can be employed as well.

Among bases suitable according to the present invention, inorganic bases, in particular mineral bases are preferred. Especially alkali metal carbonates and/or bicarbonates are advantageously used to facilitate uptake reaction of the formed hydracid. Especially preferred are sodium carbonate and/or bicarbonate. Mixtures of bases can be employed as well.

It is advisable to perform the reaction at an elevated temperature, preferably at the boiling temperature of the mixture.

According to the present invention the resulting (−)-trans-N-p-fluorobenzoylmethyl-4-(p-fluorophenyl)-3-[[3,4-(methylenedioxy)phenoxy]methyl]-piperidine, i.e. the free base form, can be converted to a pharmaceutically acceptable addition salt. Advantageously, the acid corresponding to the desired addition salt is reacted with said free base. Among the pharmaceutically acceptable salts, the hydrochloride is preferred. Therefore, hydrochloric acid is preferably employed in the process according to the present invention.

According to the present process either the free base or a pharmaceutically acceptable addition salt thereof can be isolated. Preferably, a salt is isolated which can be conveniently achieved by its simple precipitation from the reaction mixture. Optionally, the resulting product may be crystallized from a suitable solvent or solvent mixture, such as acetonitrile/diethyl ether.

The following example serves to illustrate the present invention without limiting it.

EXAMPLE 1

(−)-trans-N-p-fluorobenzoylmethyl-4-(p-fluorophenyl)-3-[[3,4-(methylenedioxy)phenoxy]methyl]-piperidine hydrochloride 88.3 g (0.22 mole) of (−)-trans-(p-fluorophenyl)-3-[[3,4-(methylenedioxy)phenoxy]methyl]-piperidine acetate (European Patent 223403) were dissolved in 700 ml of 96° ethanol. Then 70,2 g of sodium bicarbonate (0.836 mole) and 49.4 g of 2-chloro-4'-fluoroacetophenone (0.286 mole) were added. The mixture was refluxed for 90 minutes. After cooling, the inorganic salts were filtered and the solid was washed with small volumes of 96% ethanol. The liquid phase was evaporated to dryness. The resin obtained was dissolved in 500 ml of diethyl ether, the solid formed was filtered and the liquid was carefully poured, under vigorous stirring, onto a mixture containing 800 ml of 4M hydrochloric acid and 1.1 l of diethyl ether. The mixture was stirred for 1 hour. The resultant solid was washed with 800 ml of distilled water and crystallized from acetonitrile:diethyl ether (1:5, v/v). 95.3 g (yield: 88%) of crystalline solid were obtained as needles corresponding to (−)-trans-N-p-fluorobenzoyl-methyl-4-(p-fluorophenyl)-3-[[3,4-(methylenedioxy)phenoxy]methyl]-piperidine hydrochloride. 99.7% purity was determined by HPLC.

$[\alpha]_D$ at 0.5% (ethanol): −54°. IR (KBr) and $^1$H-NMR (DMSO) spectra, elemental analysis and melting point were in agreement with those of the sample obtained in the Example 1 of Patent Application No. P9400582. The increase in the $[\alpha]_D$ value was due to the enhanced purity of the present sample.

We claim:
1. A process for preparing (−)-trans-N-p-fluorobenzoylmethyl-4-(p-fluorophenyl)-3-[[3,4-(methylenedioxy)phenoxy]methyl]-piperidine, as well as pharmaceutically acceptable addition salts thereof, which comprises reacting (−)-trans-(p-fluorophenyl)-3-[[3,4-(methylenedioxy)phenoxy]methyl]-piperidine acetate with 2-chloro- or 2-bromo-4'-fluoroacetophenone in an alkanol having one to four carbon atoms and in the presence of a base at an elevated temperature of the mixture, and, if desired, converting the resulting compound to a pharmaceutically acceptable addition salt by reaction with the corresponding acid.

2. A process as claimed in claim 1 wherein said 2-chloro- or 2-bromo-4'-fluoroacetophenone is 2-chloro-4'-fluoroacetophenone.

3. A process as claimed in claim 1 or claim 2 wherein the alkanol having one to four carbon atoms is methanol and ethanol.

4. A process as claimed in claim 1 wherein the corresponding acid is hydrochloric acid.

5. A process as claimed in claim 1 wherein (−)-trans-N-p-fluoro-benzoylmethyl-4-(p-fluorophenyl)-3-[[3,4-(methylenedioxy)phenoxy]methyl]-piperidine is isolated as a pharmaceutically acceptable salt, preferably as hydrochloride.

6. A process as claimed in claim 1, wherein the base is a mineral base.

7. A process as claimed in claim 6, wherein the mineral base is an alkali metal carbonate and/or bicarbonate.

8. A process as claimed in claim 1, wherein the reaction is carried out at the boiling temperature of the mixture.

* * * * *